United States Patent
Naeff et al.

(10) Patent No.: US 7,378,519 B2
(45) Date of Patent: May 27, 2008

(54) ADDUCT OF TOPIRAMATE AND TRAMADOL HYDROCHLORIDE AND USES THEREOF

(75) Inventors: Rainer Naeff, Schlatt (CH); Sonja Spycher-Huber, Benken (CH); Thomas Hunziker, Schaffhausen (CH); Guenter Laufer, Singen (DE)

(73) Assignee: Cilag GmbH International, Schaffhausen (CH)

( * ) Notice: Subject to any disclaimer, the term of this patent is extended or adjusted under 35 U.S.C. 154(b) by 0 days.

(21) Appl. No.: 10/514,739

(22) PCT Filed: May 16, 2003

(86) PCT No.: PCT/EP03/05321

§ 371 (c)(1),
(2), (4) Date: Jan. 11, 2006

(87) PCT Pub. No.: WO03/099273

PCT Pub. Date: Dec. 4, 2003

(65) Prior Publication Data

US 2006/0234949 A1   Oct. 19, 2006

(30) Foreign Application Priority Data

May 23, 2002   (EP) .................................. 02077019

(51) Int. Cl.
*C07H 1/06* (2006.01)
*C07C 215/00* (2006.01)

(52) U.S. Cl. .................... 536/127; 536/122; 564/355
(58) Field of Classification Search ................ 514/23, 514/456, 643, 646; 536/54, 120, 127
See application file for complete search history.

(56) References Cited

U.S. PATENT DOCUMENTS

| | | | | |
|---|---|---|---|---|
| 3,652,589 | A | * | 3/1972 | Flick et al. .................. 548/578 |
| 4,513,006 | A | * | 4/1985 | Maryanoff et al. ............ 514/23 |
| 5,336,691 | A | * | 8/1994 | Raffa et al. .................. 514/629 |
| 5,468,744 | A | * | 11/1995 | Raffa et al. .................. 514/282 |
| 5,516,803 | A | * | 5/1996 | Raffa .......................... 514/570 |
| 6,562,865 | B1 | * | 5/2003 | Codd et al. .................. 514/456 |
| 2002/0156133 | A1 | | 10/2002 | Bartholomaeus et al. |
| 2003/0158242 | A1 | | 8/2003 | Kugelmann |

FOREIGN PATENT DOCUMENTS

| | | |
|---|---|---|
| DE | 19927689 A1 | 12/2000 |
| DE | 19940740 A1 | 3/2001 |
| WO | WO 01/13904 A2 | 3/2002 |

OTHER PUBLICATIONS

PCT Search Report for International Application No. PCT/EP03/05321 dated Sep. 11, 2003.

* cited by examiner

*Primary Examiner*—S. Anna Jiang
*Assistant Examiner*—L. E. Crane

(57) ABSTRACT

Processes for isolation and purification of enantiomerically enriched compositions comprising tramadol and topiramate, and also for the subsequent isolation of 1S,2S-tramadol hydrochloride, are disclosed herein.

1 Claim, No Drawings

ADDUCT OF TOPIRAMATE AND TRAMADOL HYDROCHLORIDE AND USES THEREOF

This application is a 371 of PCT/EP03/05321, filed May 16, 2003, which claims priority from EPO Application No. 02077019.4, filed May 16, 2002.

BRIEF DESCRIPTION OF THE INVENTION

This invention relates to a new pharmaceutically useful compound, which is a stoichiometrically 1:1 adduct of tramadol hydrochloride and topiramate, and to the manufacture and use thereof.

BACKGROUND OF THE INVENTION

A number of effective anticonvulsants including the compound 2,3:4,5-bis-O-(1-methylethylidene)-β-D-fructopyranose sulfamate, also known as topiramate, have been disclosed in U.S. Pat. No. 4,513,006. Topiramate is useful in the treatment of human epilepsy in that it is effective as adjunctive therapy or as monotherapy in treating simple and complex partial seizures and secondarily generalized seizures (E. Faught et. al., Epilepsia 36 (S4) 33, 1995; S. K. Sachdeo, et al., Epilepsia 36 (S4) 33, 1995). Topiramate is currently marketed for the treatment of simple and complex partial seizure epilepsy with or without secondary generalized seizures.

Recent preclinical studies on topiramate have revealed previously unrecognized pharmacological properties which suggest that topiramate is effective in treating some other disorders. One of these is neuropathic pain. Neuropathic pain remains one of the "frontiers" of pain management. There is a significant unmet need for efficacious and tolerable pharmacotherapy, making neuropathic pain an area of intense research interest. The term "neuropathic pain" is applied to any acute or chronic pain syndrome in which the sustaining mechanism for the pain is believed to involve abnormal transmission (peripheral) or processing (central) of somatosensory input. U.S. Pat. No. 5,760,007 discloses topiramate as useful for the treatment of neuropathic pain.

A class of analgesic cycloalkanol-substituted phenol esters having a basic amine group in the cycloalkylring, are disclosed in U.S. Pat. No. 3,652,589. Among these is the compound (1R,2R or 1S,2S)-2-[(dimethylamino)methyl]-1-(3-methoxyphenyl)-cyclohexan-1-ol, generically designated as tramadol, which is specifically disclosed therein. Tramadol typically is used as the hydrochloride salt form.

A series of articles pertaining to the pharmacology, toxicology and clinical studies of tramadol hydrochloride are found in Arzneim. Forsch., (Drug Res.), 1978, 28(1), 114. The Abstracts of the VI th World Congress on Pain, Apr. 1-6 (1990), disclose that tramadol hydrochloride is an orally active pure agonist opioid analgesic. However, clinical experience indicates that tramadol hydrochloride lacks many of the typical side effects of opioid agonists. Tramadol hydrochloride's 'atypical' combination of non-opioid and opioid activity makes tramadol a very unique drug. Tramadol hydrochloride is currently marketed as an analgesic.

Opioids have for many years been used as analgesics to treat severe pain. They, however, produce undesirable side effects such as respiratory depression, constipation, tolerance and abuse liability, and, as a result, cannot always be given repeatedly or at high doses.

To reduce the side effect problems, opioids have been combined with other drugs, including non-opioid analgesic agents, which lower the amount of opioid needed to produce an equivalent degree of analgesia. It has been claimed that some of these combination products also have the advantage of requiring less of each ingredient while producing a synergistic analgesic effect.

As an analgesic, tramadol hydrochloride has been combined with both opioid and non-opioid analgesic drugs. Such compositions have exhibited synergistic effects in treating pain while using less of each ingredient to produce an equivalent degree of analgesia. Specifically, U.S. Pat. No. 5,516,803 discloses the composition of tramadol hydrochloride and a NSAID, particularly ibuprofen. U.S. Pat. No. 5,468,744 discloses tramadol hydrochloride plus any of oxycodone, codeine or hydrocodone and U.S. Pat. No. 5,336,691 discloses tramadol hydrochloride in combination with acetaminophen.

WO-01/13904 is concerned with a pharmaceutical composition comprising a combination of a tramadol material and an anticonvulsant drug and to the pharmacological use of the composition in treating conditions of pain and neurologic or psychiatric disorders. The composition produces a combination product having improved properties, requiring less of each ingredient and producing a synergistic effect.

WO-01/13904 further discloses that in animal studies using the Chung model of post-nerve constriction injury, both tramadol hydrochloride and topiramate are significantly active and reach 100% MPE (Maximum Possible Effect) as the dose is escalated. When topiramate and tramadol hydrochloride are co-administered in this model the $ED_{50}$ of both drugs is dramatically reduced, suggesting synergy of analgesic effect. The degree of synergy varies across ratios in this model with those ratios in which tramadol hydrochloride predominates displaying the greatest synergy.

Compositions including combinations of topiramate and tramadol hydrochloride have been found to be relatively unstable, in particular due to the instability of topiramate. It is therefore a desirable goal to provide combination formulations of topiramate and tramadol hydrochloride that are stable.

Moreover, the half lives of topiramate and tramadol are largely different in that tramadol's half life is relatively short while that of topiramate is relatively longer. Plasma levels of tramadol therefore will sink more rapidly below effectivity thresholds than those of topiramate, which is undesirable because there is a need to keep the blood plasma levels of both active ingredients at a sufficient level, in particular during a relatively long period of time. Therefore there is a need to provide pharmaceutical compositions that release both topiramate and tramadol at a sufficient level, during a sufficiently long period of time. The present invention provides an adduct of topiramate and tramadol, which allows the preparation of pharmaceutical compositions that meet this need.

SUMMARY OF THE INVENTION

This invention relates to a chemical compound which is an adduct of tramadol hydrochloride and topiramate. This adduct can be represented by the following chemical structure:

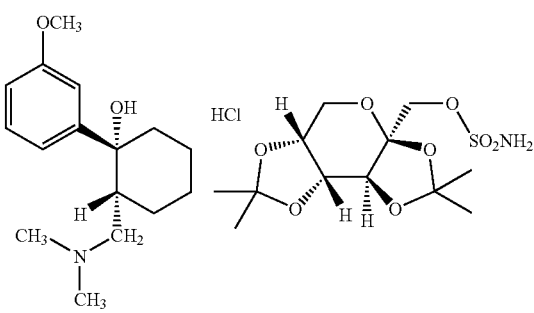

(I)

1R,2R-tramadol hydrochloride  Topiramate

The adduct in particular is the 1:1 adduct.

In particular, the tramadol hydrochloride in the adduct is one enantiomeric form, namely (1R,2R)-2-[(dimethylamino)methyl]-1-(3-methoxyphenyl)-cyclohexan-1-ol hydrochloride or 1R,2R-tramadol hydrochloride.

In another aspect the invention concerns a process for manufacturing the 1:1 adduct of tramadol hydrochloride and topiramate of formula (I) comprising crystallizing the 1:1 adduct from a suitable solvent.

In still another aspect, the invention provides a process for preparing enantiomerically pure tramadol hydrochloride. The (1S,2S)-2-[(dimethylamino)methyl]-1-(3-methoxyphenyl)-cyclohexan-1-ol hydrochloride enantiomer, i.e. 1S,2S-tramadol hydrochloride, remains in the mother liquor when crystallizing the 1:1 adduct.

The (1R,2R)-2-[(dimethylamino)methyl]-1-(3-methoxyphenyl)-cyclohexan-1-ol hydrochloride enantiomer, i.e. 1R,2R-tramadol can be isolated of formula (I) by separating the 1R,2R tramadol hydrochloride from the topiramate in the adduct.

In a further embodiment, the invention relates to pharmaceutical compositions comprising an effective amount of a 1:1 adduct of tramadol hydrochloride and topiramate. The invention also provides a process for preparing said pharmaceutical formulations comprising mixing the adduct with appropriate carrier materials.

Furthermore, the invention concerns a method of treating a warm blooded animal suffering from neuropatic pain, said method comprising the administration of an effective amount of the 1:1 adduct of tramadol hydrochloride and topiramate described herein.

DETAILED DESCRIPTION OF THE INVENTION

Tramadol is the compound (1R,2R or 1S,2S)-2-[(dimethylamino)methyl]-1-(3-methoxyphenyl)-cyclohexan-1-ol. Preferably tramadol is used as a salt form, in particular its hydrochloride salt. Tramadol hydrochloride is commercially available from Grunenthal or may be made by the process described in U.S. Pat. No. 3,652,589.

Topiramate is the compound 2,3:4,5-bis-O-(1-methylethylidene)-β-D-fructopyranose sulfamate and can be prepared according to processes described in U.S. Pat. No. 4,513,006.

The adduct of formula (I) can be manufactured in its pure form by dissolving topiramate and tramadol hydrochloride at a suitable molar ratio in a suitable solvent e.g. a lower alkanol, in particular a $C_{1-3}$ alkanol such as methanol, ethanol or 1- or 2-propanol, at elevated temperature. In an embodiment of this method of manufacture, the two starting materials are dissolved in the solvent at elevated temperature, or the starting materials can be introduced in the solvent which is brought to an elevated temperature, e.g. at a temperature above 30° C., or above 40° C. In one embodiment this temperature is about 40° C. The whole is allowed to cool to temperatures below room temperature, e.g. to a temperature below 10° C., or to a temperature that is in the range of from 2-8° C., or below 0° C., for example even as low as −18° C. Cooling may be done immediately or gradually, over a certain period of time, or stepwise. The adduct crystallizes and the crystals may then be isolated from the mother liquor, e.g. by filtration.

The molar ratios of topiramate:tramadol hydrochloride used in this procedure may vary. For example molar ratios of topiramate:tramadol hydrochloride in the range of 1:1 and 1:4 can be used. Preferred are molar ratios that approximate 1:2, in one embodiment said ratio is about 1:2.

The adduct can alternatively be prepared by storing a dry powder mixture of topiramate and tramadol hydrochloride under high relative humidity at elevated temperatures for a sufficient long period of time, e.g at temperatures above 50° C. or above 60° C. for several weeks, e.g. 3, 4 or 5 weeks or more. The adduct can be isolated from the mixture following art-known procedures.

The resulting adduct is a crystalline compound that can be characterized by its melting point, X-ray diffractometry or by spectroscopic methods such as IR.

Single crystal X-ray diffractometric results showed that the crystalline adduct consists of topiramate molecular moieties and tramadol molecular moieties in a 1:1 ratio alternating in a crystal lattice with Cl⁻ ions arranged in between these two molecular moieties. The single crystal X-ray diffractometric structural analysis did not allow the determination of the exact position of any of the hydrogen atoms and consequently the position of the proton derived from the hydrogen chloride entity could not be determined. Without being bound to theory it is assumed that, given the basicity of tramadol, the hydrochoride proton is most likely coordinated to the nitrogen atom of tramadol, thus forming a tramadol —H⁺ ionic moiety.

The adduct of formula (I) is a defined compound that has attractive properties. It is a stable compound and therefore both active ingredients of which the adduct is composed are being kept stable, in particular topiramate which tends to be less stable in particular in more acid environments. Additionally, the adduct of formula (I) is a combination product of tramadol hydrochloride and topiramate wherein in particular instances the combination shows a synergy and wherein the combination provides a constant and sustained release of both active ingredients. The adduct of formula (I) additionally may find use in a method for treating conditions of pain, in particular neuropathic pain, and neurological or psychiatric disorders in mammals.

An additional feature of the present invention comprises the fact that it allows the preparation of (1S,2S)-2-[(dimethylamino)methyl]-1-(3-methoxyphenyl)-cyclohexan-1-ol hydrochloride, herein referred to as 1S,2S-tramadol hydrochloride, or enantiomerically enriched mixtures of 1S,2S-tramadol hydrochloride. Said enantiomerically enriched mixtures are mixtures of 1R,2R-tramadol hydrochloride and 1S,2S-tramadol hydrochloride in which the latter is predominantly present. In one embodiment said enantiomerically enriched mixtures contain at least about 80% (w/w, calculated relative to the total amount of tramadol hydrochloride) of 1S,2S-tramadol hydrochloride, or at least 90%, or at least 95% or even at least 98% of 1S,2S-tramadol hydrochloride.

A similar feature of the present invention comprises the fact that it allows the preparation of (1R,2R)-2-[(dimethylamino)methyl]-1-(3-methoxyphenyl)-cyclohexan-1-ol hydrochloride, herein referred to as 1R,2R-tramadol hydrochloride, or enantiomerically enriched mixtures of 1R,2R-tramadol hydrochloride. Said enantiomerically enriched mixtures are mixtures of 1S,2S-tramadol hydrochloride and 1R,2R-tramadol hydrochloride in which the latter is predominantly present. In one embodiment said enantiomerically enriched mixtures contain at least about 80% (w/w, calculated relative to the total amount of tramadol hydrochloride) of 1R,2R-tramadol hydrochloride, or at least 90%, or at least 95%, or even at least 98% of 1R,2R-tramadol hydrochloride.

These products can be isolated from the reaction products of the above described procedures to prepare the adduct of formula (I).

The 1S,2S-tramadol HCl isomer, or enantiomerically enriched mixtures thereof, can be obtained from the mother liquor when preparing the 1:1 adduct of formula (I) following the crystallization procedure described above. The crystals are filtered off and the 1S,2S-tramadol HCl is isolated by preparative chromatography or selective crystallization. If deemed necessary, prior to this isolation step, a second crystallization step may be introduced, i.e. the mother liquor is brought again to elevated temperature, optionally with the addition of additional topiramate, whereupon the whole is cooled again as described above to allow a second batch of adduct of formula (I) to crystallize.

The 1R,2R-tramadol hydrochloride isomer, or enantiomerically enriched mixtures thereof, can be obtained from the adduct of formula (I) by separating the 1R,2R-tramadol from the topiramate in the adduct.

In the latter instance, the adduct is split into its components topiramate and 1R,2R-tramadol hydrochloride. This can be accomplished by dissolving the adduct in a suitable solvent, such as a halogenated hydrocarbon, e.g. dichloromethane, chloroform and the like. The two components can be separated e.g. by preparative chromatography or by a recrystallization procedure. Alternatively, the adduct of formula (I) can be contacted with a solvent in which topiramate is not very soluble, but tramadol HCl is, e.g. a polar solvent such as water.

This can be done, for example, by stirring up a mixture of the adduct of formula (I), which has been made into small particles, in water, optionally while slightly heating. The topiramate is separated off, e.g. by filtration. The filtrate contains the desired 1R,2R-tramadol hydrochloride.

Or, the adduct of formula (I) can be subjected to an appropriate extraction procedure. In this instance, the extract contains the desired 1R,2R-tramadol hydrochloride.

The solutions containing 1R,2R-tramadol hydrochloride can be allowed to crystallize for example by evaporating a sufficient amount of water and allowing the product to crystallize upon cooling.

This procedure allows the preparation of enantiomerically pure 1R,2R-tramadol hydrochloride.

1S,2S-tramadol or 1R,2R-tramadol can be used as an active ingredient in pharmaceutical formulations which can be applied for the same indications as (1R,2R; 1S,2S)-tramadol. Preferably 1S,2S-tramadol or 1R,2R-tramadol is used in its acid-addition salt form, more preferably as a hydrohalide salt form, in particular as the hydrochloride salt form. These formulations can be prepared following the same or similar procedures as described hereinafter.

The adduct of formula (I) can be used as an active ingredient in pharmaceutical formulations. To prepare such formulations, an effective amount of the said adduct is mixed with one or more suitable carriers according to conventional pharmaceutical compounding techniques. Preferred are solid formulations for oral application such as, for example, powders, capsules and tablets. In the case of oral solid preparations, carriers such as starches, sugars, diluents, granulating agents, lubricants, binders, disintegrating agents and the like, may be used. Because of their ease in administration, tablets and capsules represent the most advantageous oral dosage unit form, in which case solid pharmaceutical carriers are obviously employed. If desired, tablets may be sugar-coated or enteric-coated by standard techniques. The pharmaceutical compositions of the present invention will generally be in the form of a dosage unit, e.g., tablet, capsule, powder, injection, teaspoonful and the like, wherein the preferred amount of each of the active ingredient to be contained therein is determined by the aforementioned ratios.

Dosage forms prepared from the adduct of formula (I) will evidently contain tramadol hydrochloride:topiramate in a 1:1 w/w ratio. In a number of instances it may be desirable to prepare formulations in which this ratio is other than 1:1. These can be prepared by adding appropriate amounts of additional tramadol hydrochloride or topiramate to the mixture. For example it can be advantageous to have an excess of tramadol, e.g. as set forth in WO-01/13904, for example tramadol:topiramate w/w ratios of 3:1 to 5:1 may be advantageous.

The pharmaceutical compositions of the present invention are useful for treating conditions of pain and certain neurological and psychiatric disorders in mammals by the administration of a composition comprising the tramadol hydrochloride/topiramate adduct of formula (I) as defined herein. Those skilled in the art of treating mammalian pain know that the types of pain experienced by mammals are varied.

Examples of conditions of mammalian pain include, but are not limited to, centrally mediated pain, peripherally mediated pain, structural or soft tissue injury related pain, progressive disease related pain and neuropathic pain states, all of which would include acute pain such as caused by acute injury, trauma or surgery; chronic pain such as caused by neuropathic conditions, diabetic peripheral neuropathy, post-herpetic neuralgia, trigeminal neuralgia, post-stroke pain syndromes or cluster or migraine headaches; and inflammatory condition pain such as caused by osteoarthritis, rheumatoid arthritis or as sequela to disease, acute injury or trauma. The composition of the present invention is also useful in the treatment of certain neurological and psychiatric disorders including, but not limited to, bipolar disorder, psychosis, post-traumatic stress disorder, social phobia, obsessive-compulsive disorder; movement disorders such as akathisia, restless leg syndrome, tardive dyskinesia or central tremor; neurodegeneration in diseases such as ischemias (acute, delayed, recovery) or degeneration of nervous system cells due to Alzheimer's disease, Parkinson's disease or surgery; particularly, open-chest surgery; and, more particularly, open-heart or bypass surgery.

EXAMPLES

Example 1

Preparation of the Adduct of Formula (I)

Two moles of tramadol hydrochloride and one mole of topiramate are mixed in ethanol and the whole is heated to 40° C. for sufficient time to allow the solid drug substances to dissolve. Subsequently the mixture is cooled to a temperature of about 2-8° C. whereupon crystals start forming. The whole is allowed to stand for several hours at that temperature allowing the formation of the remainder of the crystals. The whole is filtrated while cool and the crystals are dried. The resulting 1:1 adduct has a melting point of about 161° C. (onset temperature).

Example 2

Composition Examples

The following formulations exemplify typical pharmaceutical compositions in dosage unit form suitable for systemic or topical administration to warm-blooded animals in accordance with the present invention.

Capsules 50 g of the adduct of formula (I), 12 g sodium lauryl sulfate, 112 g starch, 112 g lactose, 1.6 g colloidal silicon dioxide, and 2.4 g magnesium stearate are vigorously stirred together. The resulting mixture is subsequently filled into 1000 suitable hardened gelatin capsules, each comprising 50 mg of the adduct of formula (I).

Film-coated Tablets

Preparation of Tablet Core

A mixture of 500 g of the adduct of formula (I), 2850 g lactose and 1000 g starch is mixed well and thereafter humidified with a solution of 25 g sodium dodecyl sulfate and 50 g polyvinyl-pyrrolidone (Kollidon-K 90™) in about 1000 ml of water. The wet powder mixture is sieved, dried and sieved again. Then there are added 500 g microcrystalline cellulose (Avicel) and 15 g hydrogenated vegetable oil (Sterotex™). The whole is mixed well and compressed into tablets, giving 10,000 tablets, each comprising 50 mg of the adduct of formula (I).

Coating

To a solution of 50 g methyl cellulose (Methocel 60 HG™) in 225 ml of denatured ethanol there is added a solution of 25 g of ethyl cellulose (Ethocel 22 cps™) in 750 ml of dichloromethane. Then there are added 375 ml of dichloromethane and 12.5 ml glycerin. 50 g of polyethylene glycol is molten and dissolved in 225 ml of dichloromethane. The latter solution is added to the former and then there are added 12.5 g of magnesium octadecanoate, 25 g of polyvinylpyrrolidone and 150 ml of concentrated color suspension (Opaspray K-1-2109™) and the whole is homogenized. The tablet cores are coated with the thus obtained mixture in a coating apparatus.

The invention claimed is:

1. A process for preparing enantiomerically enriched mixtures of 1S,2S-tramadol hydrochloride, comprising:
   (a) dissolving topiramate and tramadol hydrochloride in an appropriate solvent which is brought to elevated temperatures and then cooled to a temperature which is below room temperature and letting the adduct crystallize
   (b) separating the crystals from the mother liquor by filtration
   (c) separating the 1S,2S-tramadol hydrochloride from the mother liquor, further comprising isolating the 1S,2S-tramadol hydrochloride by preparative chromatography or selective crystallization.

* * * * *